(12) United States Patent
Yen et al.

(10) Patent No.: US 10,157,801 B2
(45) Date of Patent: Dec. 18, 2018

(54) DETECTING THE CLEANNESS OF WAFER AFTER POST-CMP CLEANING

(71) Applicant: Taiwan Semiconductor Manufacturing Company, Ltd., Hsin-Chu (TW)

(72) Inventors: Yu-Ting Yen, Hsin-Chu (TW); Chi-Ming Tsai, Hsin-Chu (TW); Hui-Chi Huang, Hsin-Chu (TW)

(73) Assignee: Taiwan Semiconductor Manufacturing Company, Ltd., Hsin-Chu (TW)

(*) Notice: Subject to any disclaimer, the term of this patent is extended or adjusted under 35 U.S.C. 154(b) by 0 days.

(21) Appl. No.: 14/986,905

(22) Filed: Jan. 4, 2016

(65) Prior Publication Data

US 2017/0194217 A1    Jul. 6, 2017

(51) Int. Cl.
| | | |
|---|---|---|
| *H01L 21/00* | (2006.01) | |
| *H01L 21/66* | (2006.01) | |
| *H01L 21/306* | (2006.01) | |
| *H01L 21/02* | (2006.01) | |
| *G01N 21/3563* | (2014.01) | |
| *G01N 21/65* | (2006.01) | |
| *G01N 21/59* | (2006.01) | |
| *G01N 15/02* | (2006.01) | |
| *G01N 21/53* | (2006.01) | |
| *G01N 21/55* | (2014.01) | |
| *G01N 21/94* | (2006.01) | |
| *G01N 21/95* | (2006.01) | |
| *G01N 21/35* | (2014.01) | |
| *G01N 15/14* | (2006.01) | |
| *G01N 15/00* | (2006.01) | |

(52) U.S. Cl.
CPC .......... *H01L 22/12* (2013.01); *G01N 15/0211* (2013.01); *G01N 15/1459* (2013.01); *G01N 21/3563* (2013.01); *G01N 21/53* (2013.01); *G01N 21/55* (2013.01); *G01N 21/59* (2013.01); *G01N 21/65* (2013.01); *G01N 21/94* (2013.01); *G01N 21/9501* (2013.01); *H01L 21/02057* (2013.01); *H01L 21/30625* (2013.01); *G01N 2015/0053* (2013.01); *G01N 2015/0222* (2013.01); *G01N 2015/1486* (2013.01); *G01N 2015/1493* (2013.01); *G01N 2021/3568* (2013.01); *G01N 2021/3595* (2013.01)

(58) Field of Classification Search
CPC .......... H01L 21/3212; H01L 21/76883; H01L 22/12; H01L 21/30625; H01L 21/02057; H01L 21/3563; G01N 21/3563; G01N 21/65; G01N 21/59; G01N 15/0211; G01N 21/53; G01N 21/55; G01N 21/94
See application file for complete search history.

(56) References Cited

U.S. PATENT DOCUMENTS 5,922,606 A * 7/1999 Jenkins ............ H01L 21/02052
                                                  134/1.3
6,200,899 B1 * 3/2001 Fournier .......... H01L 21/02074
                                                  257/E21.304

(Continued)

*Primary Examiner* — Richard Booth
(74) *Attorney, Agent, or Firm* — Slater Matsil, LLP

(57) ABSTRACT

A method includes performing Chemical Mechanical Polish (CMP) on a wafer, placing the wafer on a chuck, performing a post-CMP cleaning on the wafer, and determining cleanness of the wafer when the wafer is located on the chuck.

20 Claims, 18 Drawing Sheets

(56) References Cited

U.S. PATENT DOCUMENTS

| | | | | |
|---|---|---|---|---|
| 2004/0004716 A1* | 1/2004 | Mavliev | ............ | G01N 15/1404 |
| | | | | 356/336 |
| 2006/0213538 A1* | 9/2006 | Umezawa | ................. | B08B 3/04 |
| | | | | 134/18 |
| 2006/0216197 A1* | 9/2006 | Jones | .................... | G01N 21/05 |
| | | | | 422/62 |
| 2012/0216833 A1* | 8/2012 | Wang | ............... | H01L 21/67051 |
| | | | | 134/10 |
| 2015/0000700 A1* | 1/2015 | Coxon | .............. | C11D 17/0013 |
| | | | | 134/7 |

* cited by examiner

DETECTING THE CLEANNESS OF WAFER AFTER POST-CMP CLEANING

BACKGROUND

Chemical mechanical Polish (CMP) processes are widely used in the fabrication of integrated circuits. When an integrated circuit is built up layer by layer on the surface of a semiconductor wafer, CMP processes are used to planarize the topmost layer to provide a planar surface for subsequent fabrication steps. CMP processes are carried out polishing the wafer surface against a polish pad. A slurry containing both abrasive particles and reactive chemicals is applied to the polish pad. The relative movement of the polish pad and wafer surface coupled with the reactive chemicals in the slurry allows the CMP process to planarize the wafer surface by means of both physical and chemical forces.

CMP processes can be used for the fabrication of various components of an integrated circuit. For example, CMP processes may be used to planarize inter-level dielectric layers and inter-metal dielectric layers. CMP processed are also commonly used in the formation of the copper lines that interconnect the components of integrated circuits.

After a CMP process, the surface of the wafer, on which the CMP process has been performed, is cleaned to remove residues. The residues may include organic matters and particles. In recent generations of integrated circuits, the sizes of the integrated circuit devices are reduced to a very small scale. This posts a demanding requirement to the post-CMP cleaning than for older generations of integrated circuits. For example, the sizes of the metal particles that remain after the post-CMP cleaning cannot exceed a half of the critical dimension (the gate length) of the transistors on the wafer. Obviously, with the reduction of the sizes of the integrated circuit devices, such requirement is tightened.

In the post-CMP cleaning, brushes were used to remove the residues on the wafers. After the post-CMP cleaning, wafers are inspected, for example, by determining the brightness of the cleaned wafer to determine whether there is residue left or not.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

DETAILED DESCRIPTION

Figure 1:
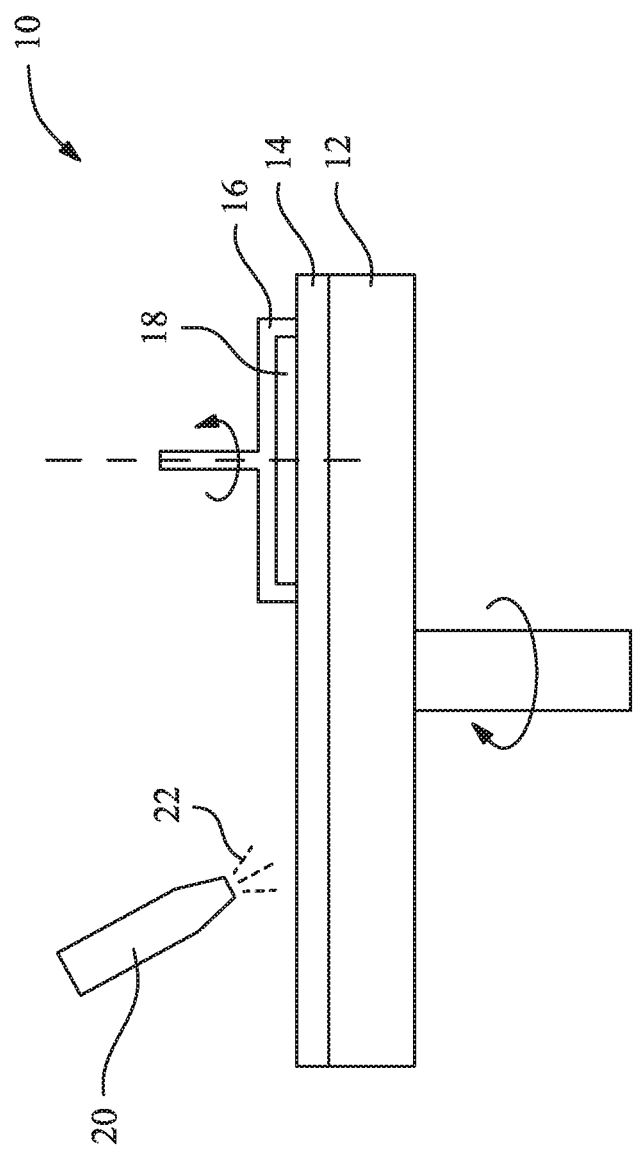
FIG. 1 illustrates Chemical Mechanical Polish (CMP) process in accordance with some embodiments.

The following disclosure provides many different embodiments, or examples, for implementing different features of the invention. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Further, spatially relative terms, such as "underlying," "below," "lower," "overlying," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly.

A process for determining the cleanness and the end point of post Chemical Mechanical Polish (CMP) cleaning is provided in accordance with various exemplary embodiments. Some variations of some embodiments are discussed. Throughout the various views and illustrative embodiments, like reference numbers are used to designate like elements.

FIGS. 1-6, 8, 10, 12, 15, 16A and 16B illustrate the cross-sectional views of intermediate stages in a CMP process and the post-CMP cleaning in accordance with some embodiments. The steps shown in 1-6, 8, 10, 12, 15, 16A and 16B are also illustrated schematically in the process flow 500 shown in FIG. 17. In the subsequent discussion, the process steps shown in of the CMP process and the post-CMP cleaning are discussed referring to the process steps in FIG. 17.

FIG. 1 schematically illustrates the CMP of a wafer in accordance with some embodiments of the present disclosure. The respective step is shown as step 502 in the process flow shown in FIG. 17. CMP system 10 includes polishing platen 12, polishing pad 14 over polishing platen 12, and polishing head 16 over polishing pad 14. Slurry dispenser 20 has an outlet directly over polishing pad 14 in order to dispense slurry onto polishing pad 14.

During the CMP, slurry 22 is dispensed by slurry dispenser 20 onto polishing pad 14. Slurry 22 includes a reactive chemical(s) that react with the surface layer of wafer 18. Furthermore, slurry 22 includes abrasive particles for mechanically polishing wafer 18.

Polishing pad 14 is formed of a material that is hard enough to allow the abrasive particles in slurry 22 to mechanically polish wafer 18, which is under polishing head 16. On the other hand, polishing pad 14 is also soft enough so that it does not substantially scratch wafer 18. During the CMP process, polishing platen 12 is rotated by a mechanism (not shown), and hence polishing pad 14 fixed thereon is also rotated along with polishing platen 12. The mechanism (such as a motor and/or a gear) for rotating polishing pad 14 is not illustrated.

During the CMP process, polishing head 16 is also rotated, and hence causing the rotation of wafer 18 fixed onto polishing head 16. In accordance with some embodiments of the present disclosure, polishing head 16 and polishing pad 14 rotate in the same direction (clockwise or counter-clockwise). In accordance with alternative embodiments, as shown in FIG. 1, polishing head 16 and polishing pad 14 rotate in opposite directions. The mechanism for rotating polishing head 16 is not illustrated. With the rotation of polishing pad 14 and polishing head 16, slurry 22 flows between wafer 18 and polishing pad 14. Through the chemical reaction between the reactive chemical in the slurry and the surface layer of wafer 18, and further through the mechanical polishing, the surface layer of wafer 18 is planarized.

After the CMP, wafer 18 is cleaned through a post-CMP cleaning step. The post-CMP cleaning step may include a plurality of steps including and not limited to, cleaning using an acidic chemical solution, cleaning using an alkaline chemical solution, cleaning using a neutral chemical solution, and rinsing with De-ionized water (DI water). The post-CMP cleaning may also include a plurality of cycles, each including a chemical solution cleaning step and a rinsing step.

Figure 2:
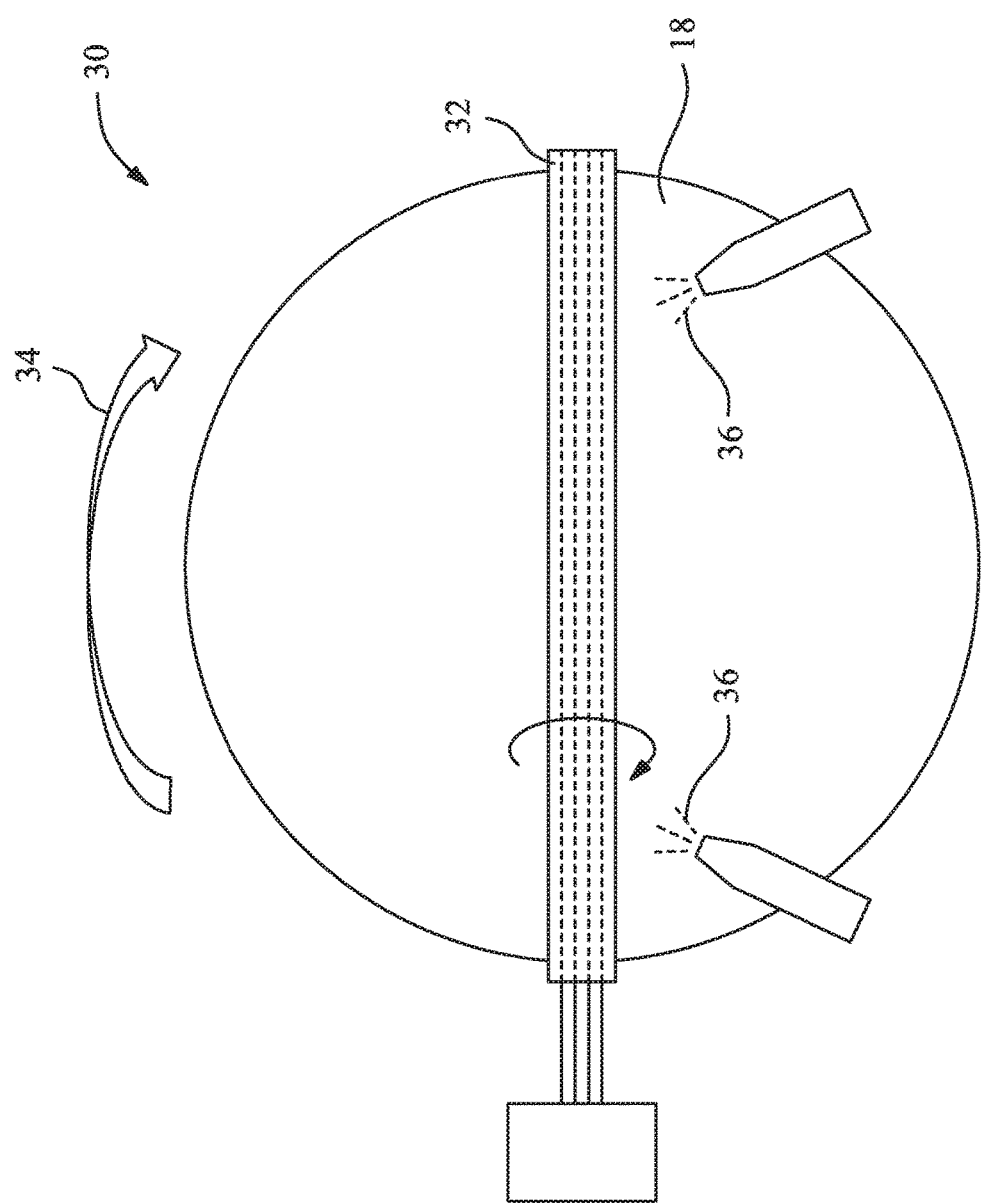
FIGS. 2 and 3 illustrate top views of wet processes in a post-CMP cleaning process in accordance with some embodiments.
Figure 3:
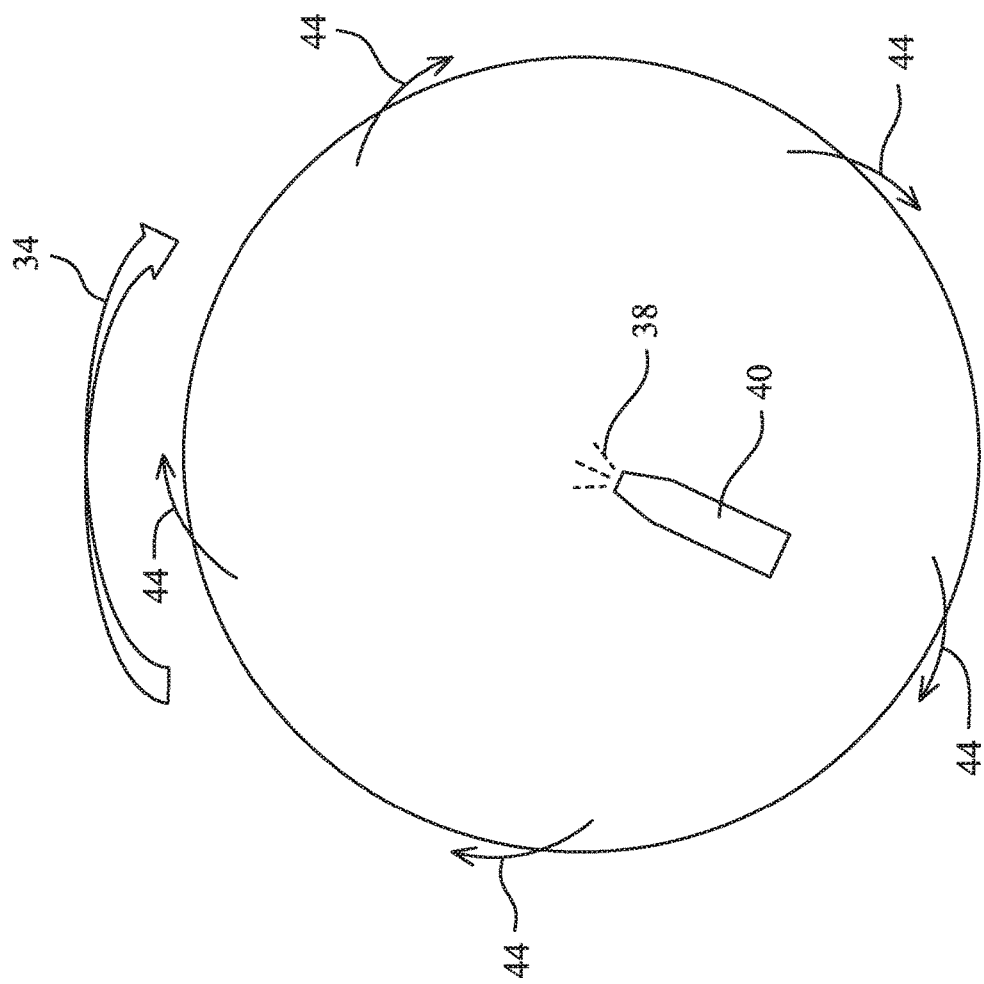

FIGS. 2 and 3 illustrate the wet processes in the post-CMP cleaning. The respective step is shown as step 504 in the process flow shown in FIG. 17. FIG. 2 illustrates a top view of the post-CMP cleaning and the respective cleaning apparatus 30 in accordance with some embodiments. Wafer 18, which has been undertaken the CMP process, has residues left on the surface of wafer 18, and the residues need to be removed from wafer 18. The residues may include organic matters and particles. In accordance with some embodiments, during the wet processes, wafer 18 is placed vertically. In accordance with alternative embodiments, wafer 18 is placed horizontally.

The cleaning apparatus 30 includes brush 32, which may be formed of Polyvinyl Alcohol (PVA), Polyvinyl chloride (PVC), Benzotriazole (BTA), or the like in accordance with some embodiments of the present disclosure. Furthermore, Brush 32 may be made to have the form of sponges. During the post-CMP cleaning process, wafer 18 is rotated, for example, as illustrated by arrow 34. In the meantime, brush 32 also rotates with respective to its own axis. The axis of brush 32 is in the lengthwise directions of the brush 32, and is parallel to the surface of wafer 18. Brush 32 has a cylindrical shape. Also, when viewed from right as shown in FIG. 2, the cross-sectional view of each of brush 32 is circular, and hence when brush 32 rotates, residues are removed from the surface of wafer 18.

During the cleaning, chemical solution (referred to as cleaning solution hereinafter) 36 is sprayed onto the surface of wafer 18. Cleaning solution 36 may include various types, and different types of cleaning solution 36 may be used to clean different residues on wafers. In accordance with some embodiments, cleaning solution 36 includes an acid chemical solution, which may include an organic acid such as citric acid, an inorganic acid such as $HNO_3$, or the like. In accordance with some embodiments, cleaning solution 36 includes an alkaline chemical solution, which may include an organic base such as $NR_3$ (with R being alkyl), an inorganic base such as $NH_4OH$, or the like. Surfactants such as sodium dodecyl sulfate may be added into cleaning solution 36 to reduce the surface tension of cleaning solution 36. Cleaning solution 36 may include water as a solvent. Cleaning solution 36 may also use organic solvents such as methanol. Cleaning solution 36 may also be an aqueous solution including peroxide. For example, cleaning solution 36 may include $H_2O_2$ in water. With the rotation of wafer 18, cleaning solution 36 is rolled into brush 32, which uses cleaning solution 36 to clean the surface of wafer 18 when brush 32 rotates. The selection of chemical solution 36 depends on the surface properties of wafer 18 such as the type of material that are expose on the surface, so that cleaning solution is able to clean the surface, and will not damage the surface. The selection of chemical solution 36 is also related to the substances used in the CMP such as the type of slurry.

FIG. 3 illustrates the rinse of wafer 18 after the cleaning using chemical solution 36. In accordance with some embodiment, wafer 18 is rinsed using DI water 38, which is sprayed onto wafer 18 by dispenser 40. During the rinse, wafer 18 is also rotated, and waste water 44 generated by the rinsing is spun off from wafer 18, and conducted away from the CMP cleaning apparatus 30.

It is appreciated that during the rinse of wafer 18, the residue such as slurry and the substance polished from wafer will be gradually removed with the proceeding of the rinsing. Furthermore, during the post-CMP cleaning, the material of brush 32 may also break apart from brush 32 and fall on wafer 18, and will be removed. With the proceeding of the rinsing, wafer 18 becomes cleaner and cleaner until at some point, the cleanness of wafer 18 is within specification, which means that the amount of the remaining residue (if any) including the particles, fall-ons, and organic materials on the surface of wafer 18 is smaller than a pre-determined acceptable amount, and the sizes of the remaining residue (if any) are also smaller than a pre-determined acceptable size.

Figure 4:
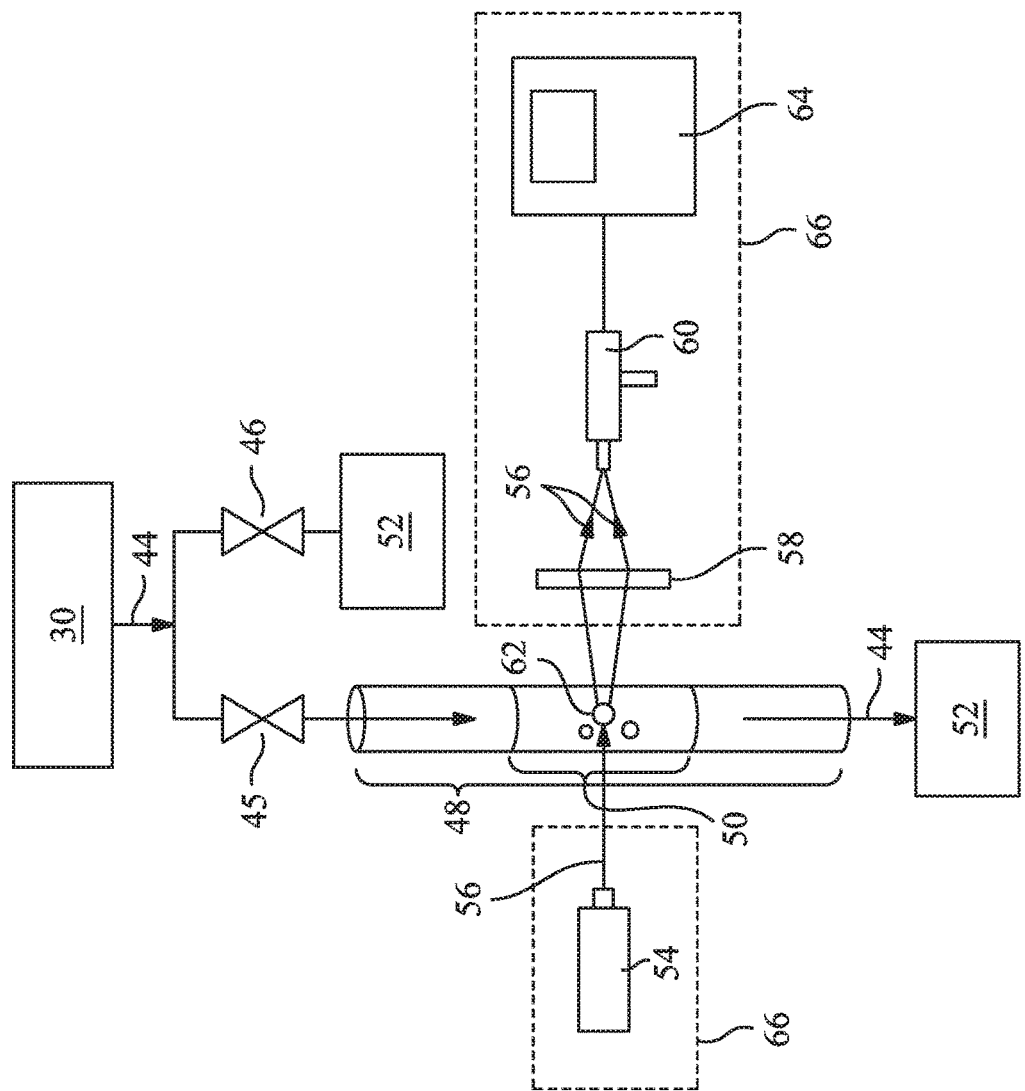
FIG. 4 illustrates determining the cleanness of a wafer using laser particle counter in accordance with some embodiments.

FIG. 4 illustrates an apparatus and a process for determining/check the cleanness of wafer 18. The respective step is shown as step 506 in the process flow shown in FIG. 17. It is expected that with the proceeding of the rinse, the waste water becomes cleaner and cleaner. The cleanness of the waste water hence reflects the cleanness of wafer 18, and the cleanness of the waste water is used to determining whether wafer 18 is clean enough. As shown in FIG. 4, CMP cleaning apparatus 30 is illustrated schematically using a box. A conduit is connected to CMP cleaning apparatus 30, and waste water 44 flows through the conduit.

In accordance with some embodiments of the present disclosure, valves 45 and 46 are connected to conduit 42. Valve 45 is connected to conduit 48, which includes transparent cell 50. Transparent cell 50 is transparent to light such as laser, and the light can pass through. Conduit 48 is further connected to waste water collecting unit 52. Valve 46 is connected to waste water collecting unit 52 with no transparent cell therebetween.

In an initial stage of the rinse process, waste water 44 includes a significant amount of the residue rinsed off from wafer 18. At this time, valve 46 is opened, and waste water 44 flows directly to waste water collecting unit 52. In the meantime, valve 45 is turned off, and hence waste water 44 does not flow through transparent cell 50. Assuming the rinse process starts at time T1, after delaying a pre-determined period of time $\Delta T$ from T1, and at time T2, valve 46 is turned off, and valve 45 is opened. Accordingly, waste water 44 flows through valve 45, transparent cell 50, and is collected by waste water collecting unit 52. The time point T2 is determined so that rinsing duration $\Delta T$, which is equal to (T2−T1), is expected to be long enough for wafer 18 to be cleaned within specification. Accordingly, it is expected that at time point T2, waste water 44 is clean enough.

In accordance with some embodiments, rinsing duration $\Delta T$ is pre-determined before the CMP of wafer 18. The determination of rinsing duration $\Delta T$ may include performing CMP on a plurality of sample wafers (not shown) that are identical to wafer 18, performing post-CMP cleaning (using the chemical solution) on the sample wafers, and then rinsing the sample wafers. All the sample wafers may be polished using the same CMP process conditions and the same post-CMP cleaning conditions. The rinsing durations, however, are different from each other for the sample wafers. Accordingly, by examining the cleanness of the sample wafers, the optimal rinsing duration $\Delta T$ can be found, wherein all wafers rinsed for rinsing duration $\Delta T$ or longer are acceptably clean (within specification). The wafers rinsed significantly shorter than rinsing duration $\Delta T$ are not clean enough (the cleanness is outside of the specification), and the wafers rinsed for periods of time shorter than, but close to, rinsing duration $\Delta T$ may or may not be clean enough.

At time point T2, with waste water 44 flowing through transparent cell 50, the number and sizes of particles in waste water 44 are determined using Laser Particle Counter (LPC) 66. Laser particle counter 66 includes laser generating unit 54 for generating laser beam 56, which is projected onto transparent cell 50. Lens 58 is placed behind transparent cell 50. Detector 60 is further placed behind lens 58 for receiving laser beam 56. When no undesirable substance is in transparent cell 50 and in the path of laser beam 56, detector 60 receives laser beam 56. When there is a particle in the path of laser beam 56, laser beam 56 is blocked and hence is not received by detector 60. The blocking durations reflects the size of the particles. Accordingly, the number of particles passing through the path of laser beam 56 determines how many times laser beam 56 is blocked, and the size of a particle determines how long laser beam 56 is blocked. Processing unit 64 is connected to detector 60, receives the signal collected by detector 60, and calculates the number and sizes of the particles.

In accordance with some embodiments of the present disclosure, a pre-determined criteria is used by processing unit 64 to determine whether waste water 44 (and wafer 18) is clean or not. The respective step is shown as step 508 in the process flow shown in FIG. 17. For example, the criteria may be the detected number (found in a unit of time) of particles that have sizes larger than a pre-determined size needs to be smaller than a pre-selected number. For example, waste water 44 is clean when in a second, the detected number particles that are larger than 500 nm is smaller than 5. If the criteria is met, the rinse is finished. Otherwise, the waste water 44 is determined as not clean, which means the surface of wafer 18 is not clean. Accordingly, the rinse needs to be prolonged. During the prolonged rinse period, waste water 44 remains to be checked periodically, until the criteria is met. At which time, the rinse process is finished. In accordance with some embodiments, if waste water 44 is not clean, the cleaning using chemical solution (FIG. 2) and the rinse are both repeated.

Figure 5:
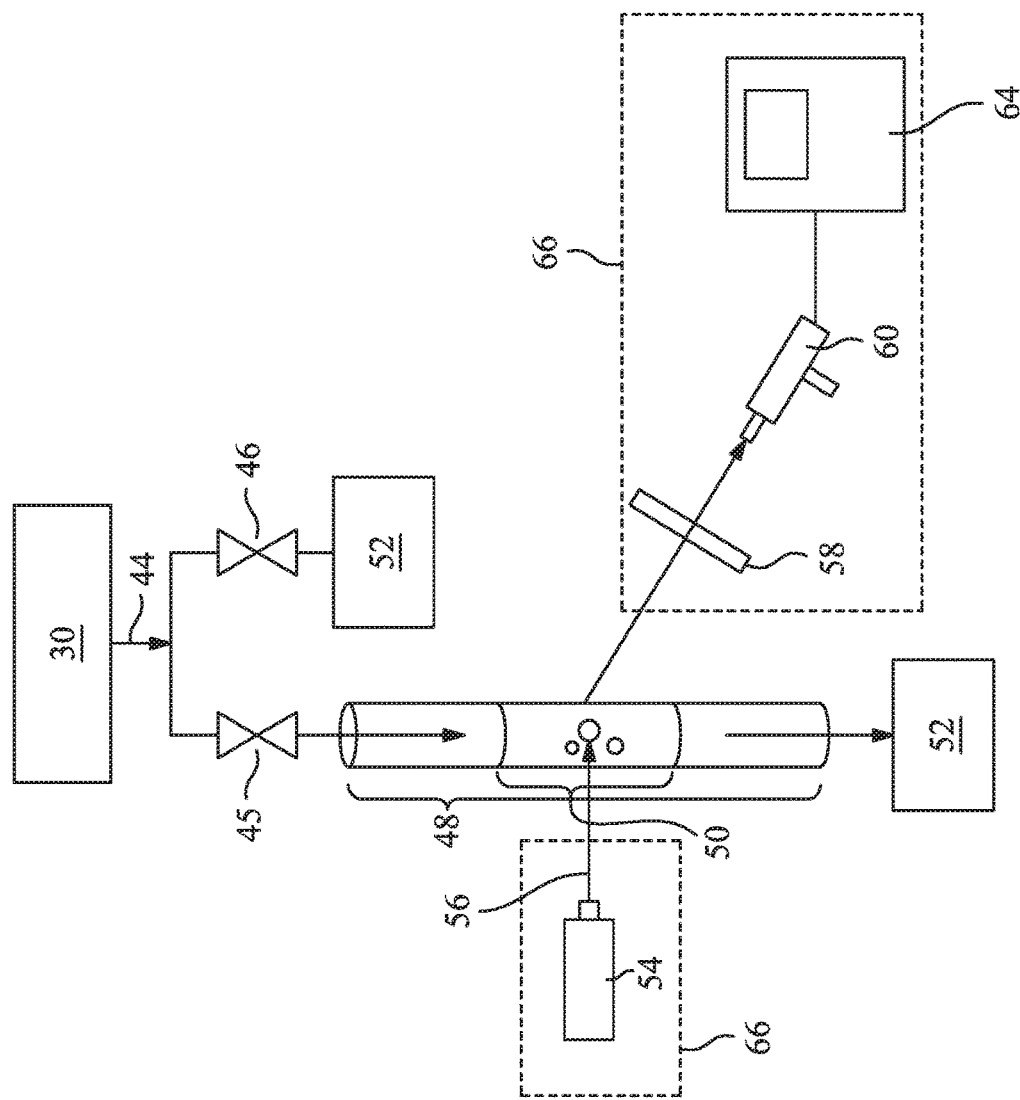
FIG. 5 illustrates determining the cleanness of a wafer using dynamic laser scattering in accordance with some embodiments.

FIG. 5 illustrates determining the number and sizes of particles using Dynamic Laser Scattering (DLS), which is used to analyze the fluctuation of the intensity of the scattered light to determine the numbers and the sizes of particles in waste water 44. The process and the apparatus for determining the cleanness of wafer 18 is essentially the same as the embodiment shown in FIG. 4, except DLS (rather than LPC) is used. In these embodiments, the detector 60 is not in the direct path of laser beam 56. The DLS and LPC are known in the art, and hence the details are not repeated herein.

After wafer 18 is determined as clean, wafer 18 is dried, for example, using a mixture of isopropanol and nitrogen ($N_2$). The respective step is shown as step 510 in the process flow shown in FIG. 17. After wafer 18 is dried, a further check may be made to determine whether wafer 18 is clean or not before wafer 18 is sent out of the CMP station. The respective step is shown as step 512 in the process flow shown in FIG. 17. If wafer 18 is clean (step 514), wafer 18 is sent out of the CMP post-CMP apparatus 30, and a subsequent wafer is sent in for the CMP and the post-CMP cleaning (step 516). Valve 45 is turned off, and valve 46 is opened for the CMP and the post-CMP cleaning of the next wafer.

Figure 6:
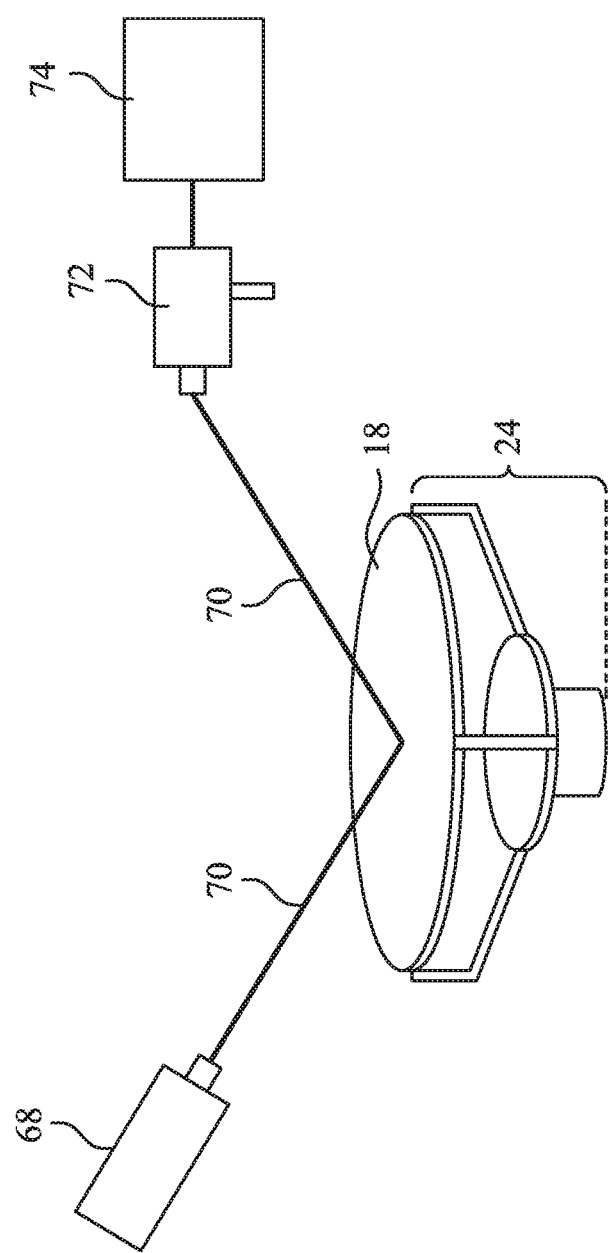
FIG. 6 illustrates determining the cleanness of a wafer using Fourier Transform Infrared Spectroscopy (FTIR) spectrum in accordance with some embodiments.
Figure 7A:
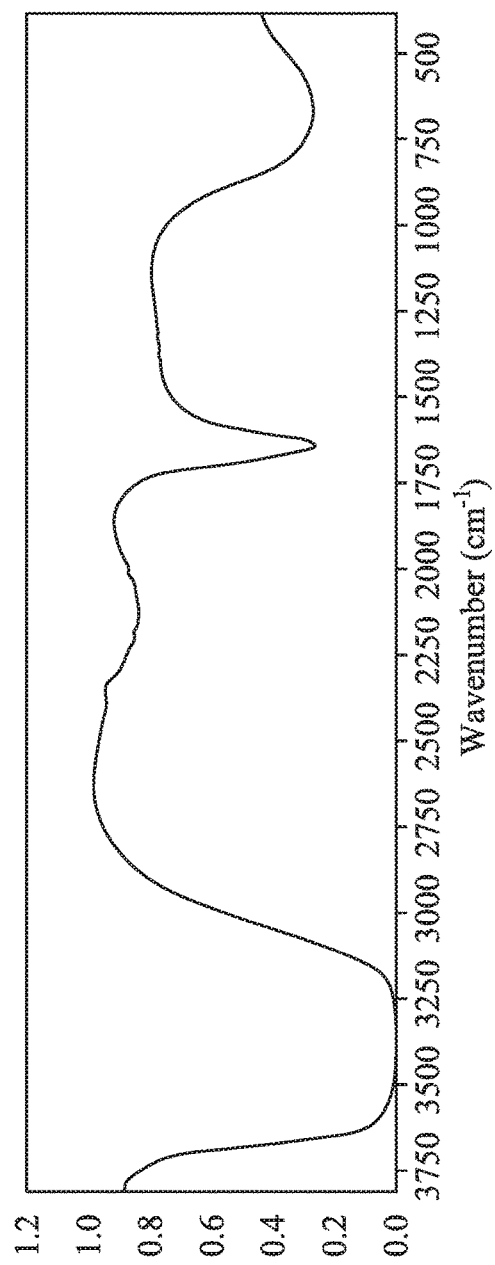
FIGS. 7A and 7B illustrate some exemplary FTIR spectrums in accordance with some embodiments.
Figure 7B:
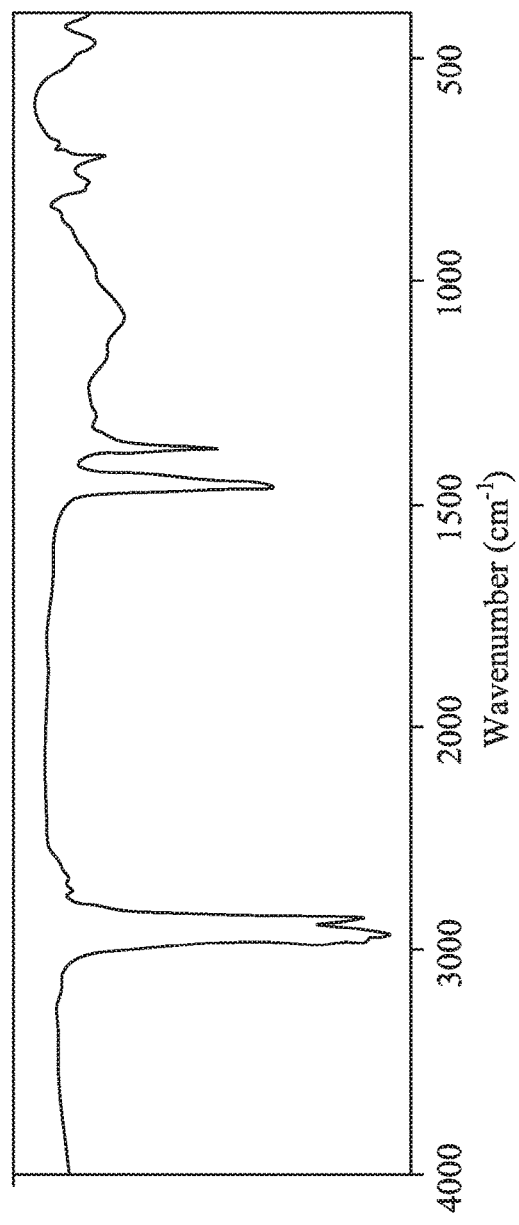

FIGS. 6, 8, 10, and 12 illustrate a plurality of methods for determining the cleanness of wafer 18 using optical analysis. It is noted that one or more of these methods may be combined with one or more of the methods shown in FIGS. 4, 5, and 15. FIG. 6 illustrates a process for determining cleanness of wafer 18 using Fourier Transform Infrared Spectroscopy (FTIR). Infrared source 68 generates infrared light 70, and projects light 70 onto wafer 18. The reflected infrared light 70 is received by detecting unit 72, which provides the received light signal to processing unit 74 to generate a FTIR spectrum. The materials on the surface of wafer 18 result in the light of different frequencies to be absorbed, and hence the resulting FTIR spectrum has characteristic peaks in response to different materials. For example, FIG. 7A illustrates the characteristic peaks of water ($H_2O$), and FIG. 7B illustrates the characteristic peaks of silicon oxide ($SiO_2$). When multiple types of materials are present at the surface of wafer 18, the combination of the characteristic peaks of the multiple materials will present in the respective FTIR spectrum. The FTIR spectrum in accordance with some embodiments covers the wavenumber ranging from 250 to 4,000 $cm^{-1}$.

Process unit 74 receives the signal from detecting unit 72, generates the FTIR spectrum, and compares the characteristic peaks in the FTIR spectrum with a database, which stores the data of the characteristic peaks of a plurality of materials that may possibly present on the surface of wafer 18. When characteristic peaks of a material(s) are found in the FTIR spectrum, processing unit 74 determines that the respective materials are present on the surface of wafer 18. For example, the characteristic peaks of $SiO_2$ are at 2,366, 1,377, 1,463, 2,855, 2,924, and 2,964 (all have unit of $cm^{-1}$ and with variation±10 $cm^{-1}$). The characteristic peaks of $Al_2O_3$ are at 2,855, 2,924, and 2,964 (all have unit of $cm^{-1}$ and with variation±10 $cm^{-1}$). The characteristic peaks of BTA are at 742, 753, 779, 1,009, 1,023, 1,210, 2,766, 2,796, and 2,870 (all have unit of $cm^{-1}$ and with variation±10 $cm^{-1}$). The characteristic peaks of PVA are at 1,098, 1,145, 1,239, 1,334, 1,497, 1,442, 1,661, 1,711, 2,837, 2,906, 2,923, and 2,945 (all have unit of $cm^{-1}$ and with variation±10 $cm^{-1}$). The characteristic peaks of PVC are at 612, 890, 835, 966, 1,098, 1,199, 1,254, 1,333, 1,428, 1,435, 2,913, and 2,970 (all have unit of $cm^{-1}$ and with variation±10 $cm^{-1}$). The characteristic peaks of silicon nitride ($Si_3N_4$) are at 1,377, 1,463, 2,852, 2,910, 2,921 (all have unit of $cm^{-1}$ and with variation±10 $cm^{-1}$).

When using FTIR to determine whether wafer 18 is clean, the characteristic peaks of water and carbon dioxide are excluded, which means the presence of the characteristic peaks of water and carbon dioxide does not necessarily mean wafer 18 is not clean. The characteristic peaks of water are at 1,640, 2,130, and 3,000~3600 (all have unit of $cm^{-1}$ and with variation±10 $cm^{-1}$). The characteristic peaks of carbon dioxide are at 665±10 $cm^{-1}$, 2,280±10 $cm^{-1}$, and 2,350±20 $cm^{-1}$. If the characteristic peaks of some materials that should not be at the surface material of wafer 18 are found, it indicates residue has been found. For example, BTA, PVA, or PVC is the material of brush 32 (FIG. 2), and when the characteristic peaks of these materials are found in the FTIR spectrum, it indicates the particles fell from brush 32 is not cleaned. Aluminum oxide and silicon oxide may be the abrasive of slurry, and if their characteristic peaks are in the FTIR spectrum, and the intended surface material of wafer 18 does not include these materials, it indicates the slurry is not cleaned, and wafer 18 needs to be cleaned again.

Figure 8:
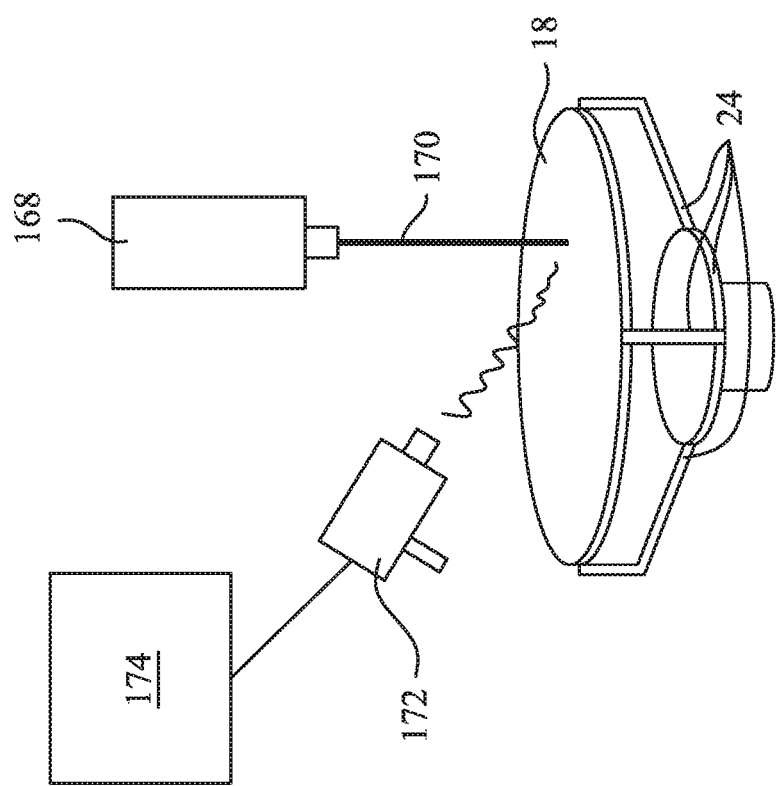
FIG. 8 illustrates determining the cleanness of a wafer using Raman spectrum in accordance with some embodiments.
Figure 9A:
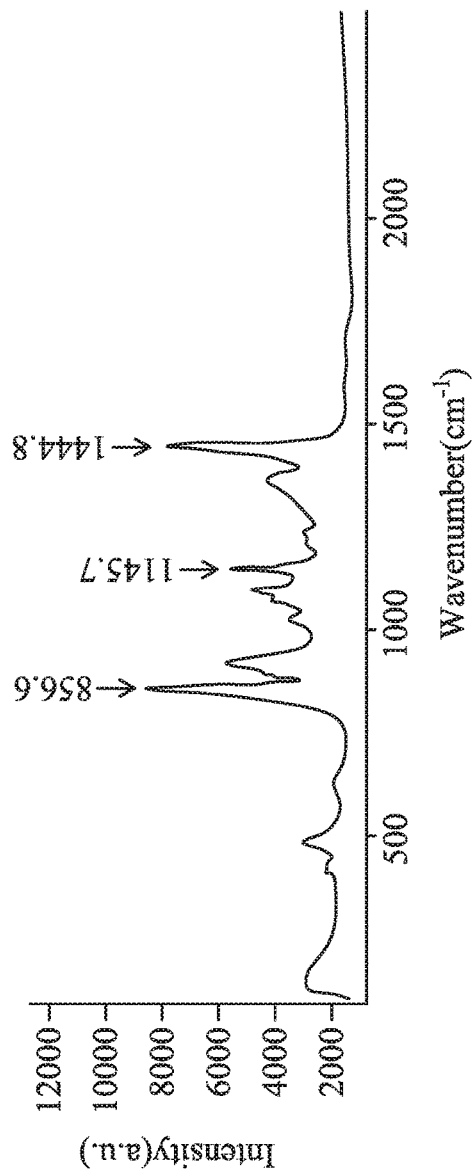
FIGS. 9A and 9B illustrate some exemplary Raman spectrums in accordance with some embodiments.
Figure 9B:
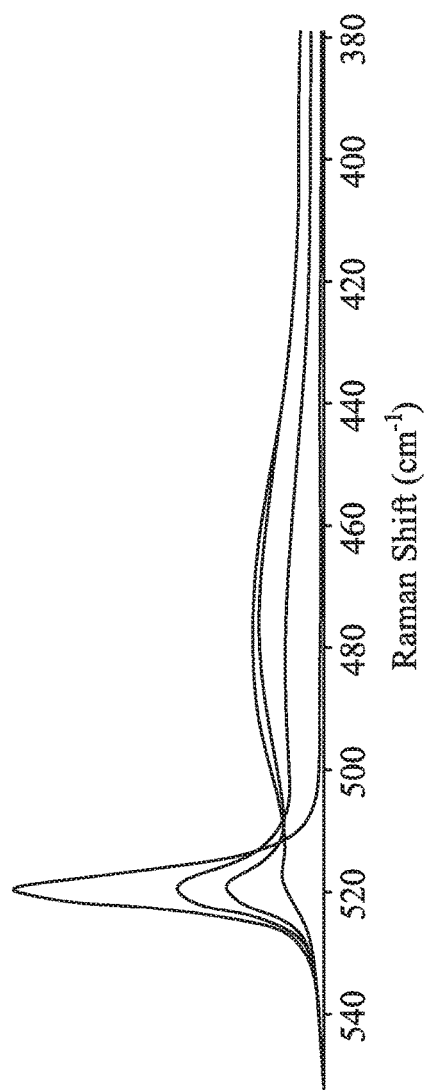

FIG. 8 illustrates determining the cleanness of the surface of wafer 18 using Raman spectrum in accordance with some embodiments. Laser source 168 generates laser 170, and projects laser 170 onto wafer 18. The reflected laser 170 is received by detecting unit 172 and processing unit 174, which generates a Raman spectrum. The materials on the surface of wafer 18 result in the resulting Raman spectrum to have a plurality of characteristic peaks. For example, FIG. 9A illustrates the characteristic peaks of PVA, and FIG. 9B illustrates the characteristic peaks of silicon. When multiple types of materials are present at the surface of wafer 18, the combination of the characteristic peaks of the respective materials will present in the respective Raman spectrum. The Raman spectrum covers the wavenumber ranging from 250 to 4,000 $cm^{-1}$.

When using Raman spectrum to determine whether wafer 18 is clean, the characteristic peaks of water are excluded. The characteristic peaks of water are at 1,640, 3,420, and 3,630 (all have unit of $cm^{-1}$ and with variation±10 $cm^{-1}$). The characteristic peak of Si is at 520±10 $cm^{-1}$. The characteristic peaks of $Al_2O_3$ are at 383 and 421 (all have unit of $cm^{-1}$ and with variation ±10 $cm^{-1}$). The characteristic peaks of BTA are at 533, 796, 1,039, 1,425, 1,567, 1,752, 1,870, 3,303, and 3,330 (all have unit of $cm^{-1}$ and with variation ±10 $cm^{-1}$). The characteristic peaks of PVA are at 633, 887, 1,023, 1,145, 1,445, 1,733, 2,940, and 2,973 (all have unit of $cm^{-1}$ and with variation ±10 $cm^{-1}$). The characteristic peaks of PVC are at 360, 634, 693, 962, 1,108, 1,175, and 1,253 (all have unit of $cm^{-1}$ and with variation ±10 $cm^{-1}$). The characteristic peaks of silicon nitride ($Si_3N_4$) are at 465, 512, 826, and 860 (all have unit of $cm^{-1}$ and with variation ±10 $cm^{-1}$).

Process unit 174 receives the signal from detecting unit 172, generates the Raman spectrum, and compares the characteristic peaks of the Raman spectrum with a database, which stores the data of the characteristic peaks of a plurality of materials that may possibly present on the surface of wafer 18. The determination of the cleanness using the characteristic peaks of Raman spectrum is similar to using FTIR spectrum, and hence is not repeated herein. If wafer 18 is found not clean, it will be cleaned again, as shown by step 514 in FIG. 17.

Figure 10:
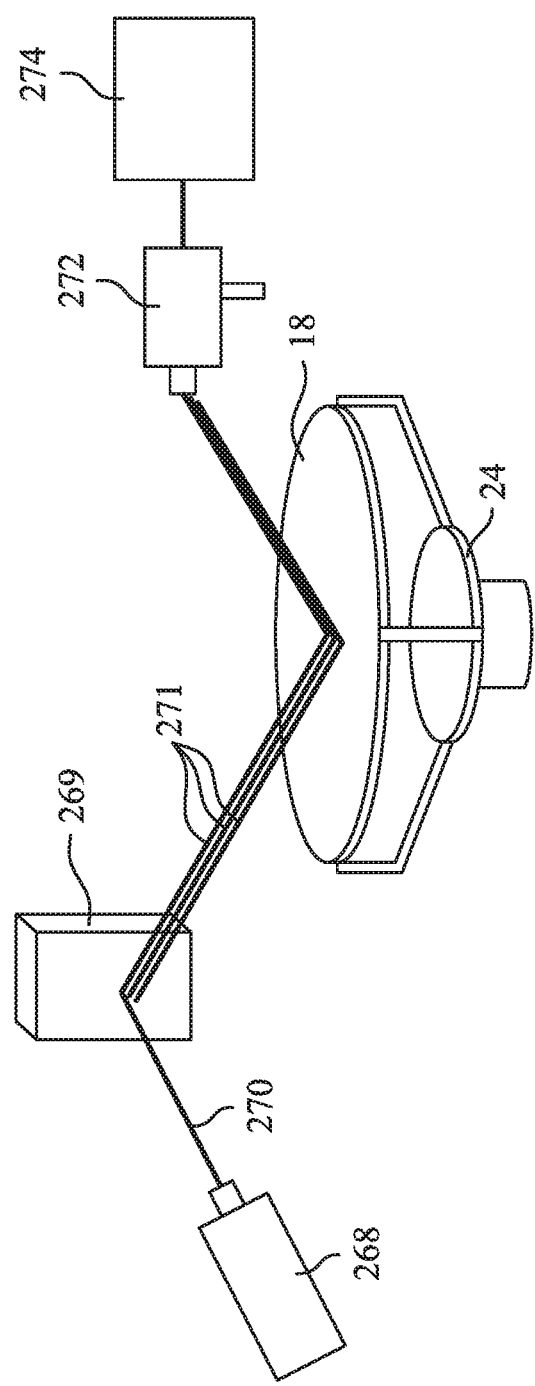
FIG. 10 illustrates determining the cleanness of a wafer using spectrometer in accordance with some embodiments.
Figure 11:
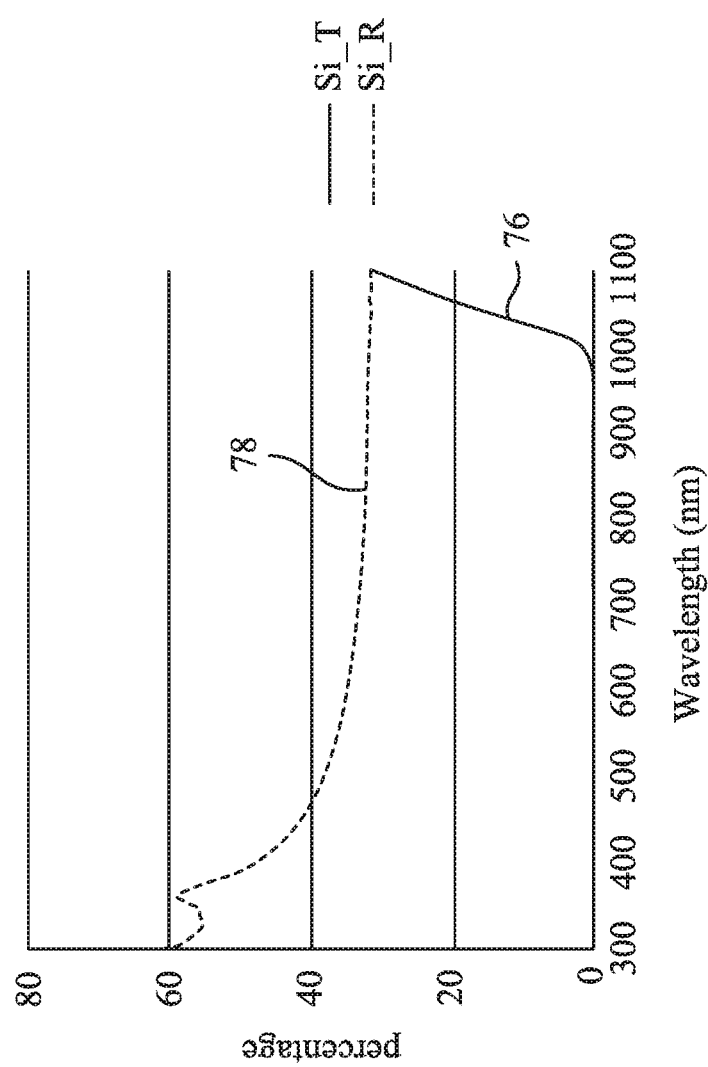
FIG. 11 illustrates exemplary transmittance and reflectance graphs of silicon in accordance with some embodiments.

In accordance with some embodiments of the present disclosure, spectrometer is used to measure the reflectance, transmittance, and the polarization sate of a light, and to determine the cleanness of wafer 18. The wavelength that may be used for determining the cleanness of wafers may be in the range between about 300 nm and about 1,100 nm. Referring to FIG. 10, light source 268 generates light 270. Diffraction grating 269 deflects light 270 as deflected light 271, which is projected onto wafer 18. The deflected light 271 is received by detecting unit 272 and processing unit 274, which generates a graph showing the transmittance and reflectance of the surface material of the measured wafer. For example, FIG. 11 illustrates the transmittance of silicon as line 76, and the reflectance of silicon as line 78. If the intended surface material of wafer 18 has residues, the transmittance and reflectance will reflect the respective residues.

In accordance with some embodiments of the present disclosure, a clean wafer (which is identical to wafer 18) may be measured using spectrometer to generate respective reference transmittance and reflectance. If residues are present at the surface of wafer 18, the transmittance and reflectance will deviate from the reference transmittance and reflectance, and hence comparing the transmittance and reflectance of wafer 18 with the reference transmittance and reflectance will reveal whether residue exists or not. For example, if an organic residue it present on the surface of wafer 18, the respective reflectance value will be lower than the reference reflectance value since the organic residue may absorb some of the light or lead to more scattering.

Figure 12:
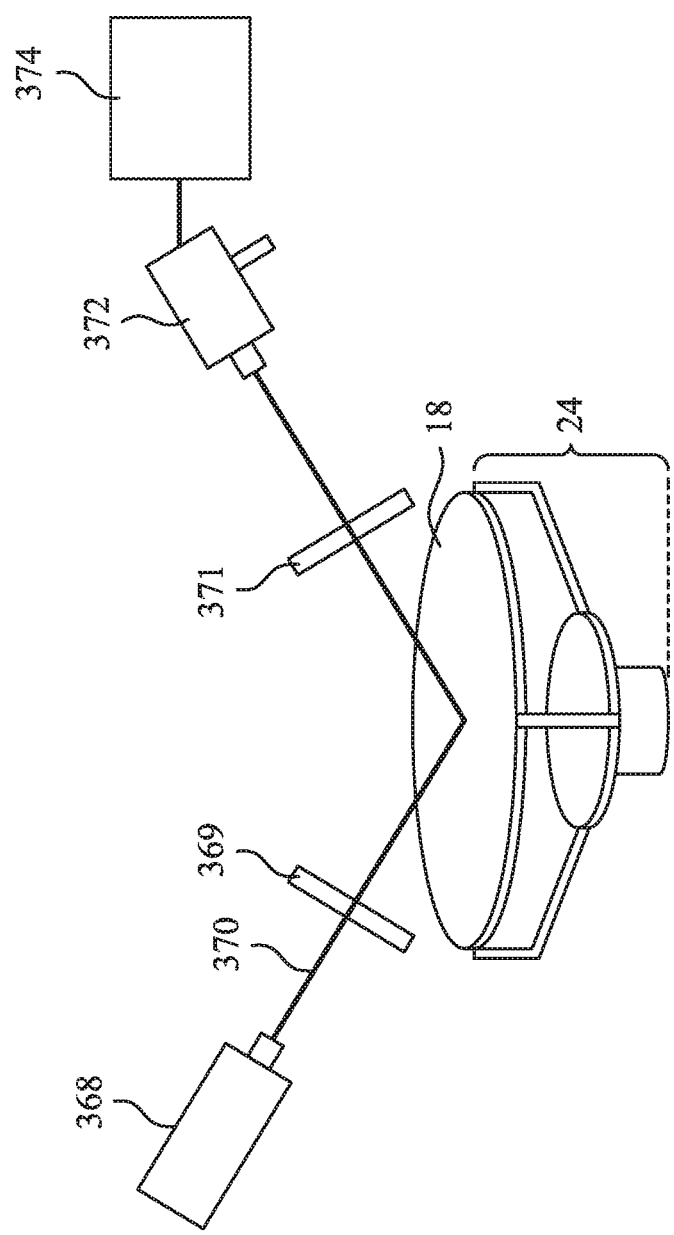
FIG. 12 illustrates determining the cleanness of a wafer using ellipsometer in accordance with some embodiments.

In accordance with some embodiments of the present disclosure, ellipsometry is used to evaluate the complex dielectric function of thin films, and to determine the cleanness of wafer 18. Referring to FIG. 12, light source 368 generates light 370, which passes through polarizer 369, reflects from wafer 18, passes through analyzer 371, and is received by detecting unit 372 and processing unit 374. Processing unit 374 generates a graph showing the w parameter (amplitude) and the Δ parameter (phase difference) of the respective complex reflectance ratio ρ. The wavelength that may be used for determining the cleanness in accordance with some embodiments may be in the range from about 200 nm to about 1,600 nm.

Figure 13:
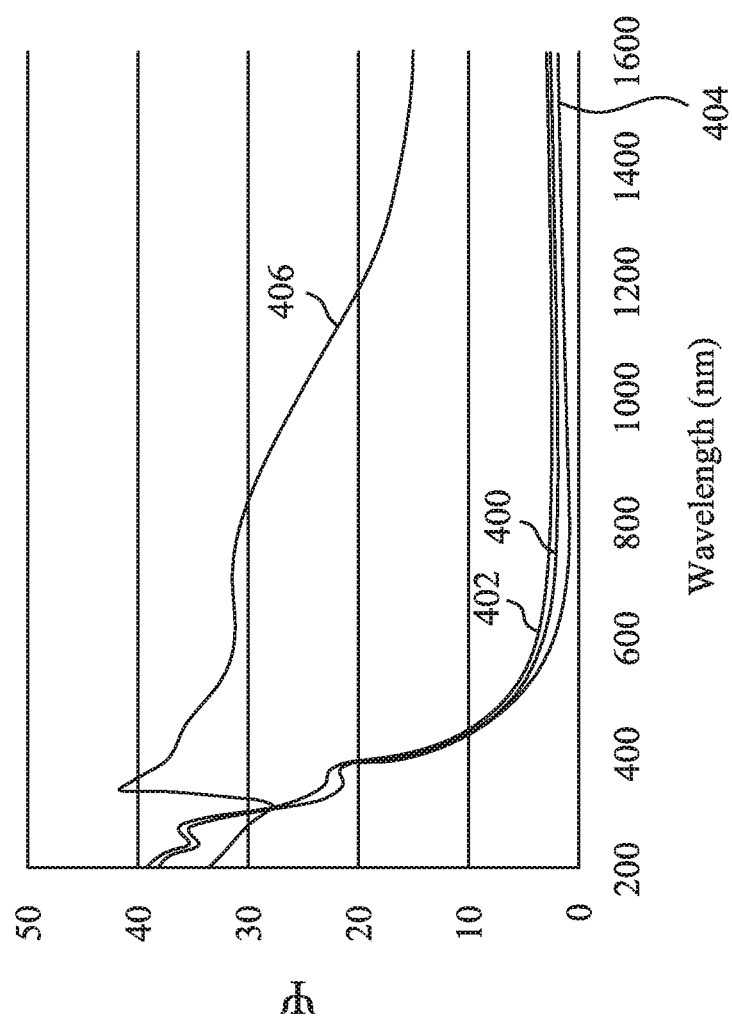
FIGS. 13 and 14 illustrate exemplary amplitude and phase difference, respectively, of some exemplary wafer surfaces in accordance with some embodiments.
Figure 14:
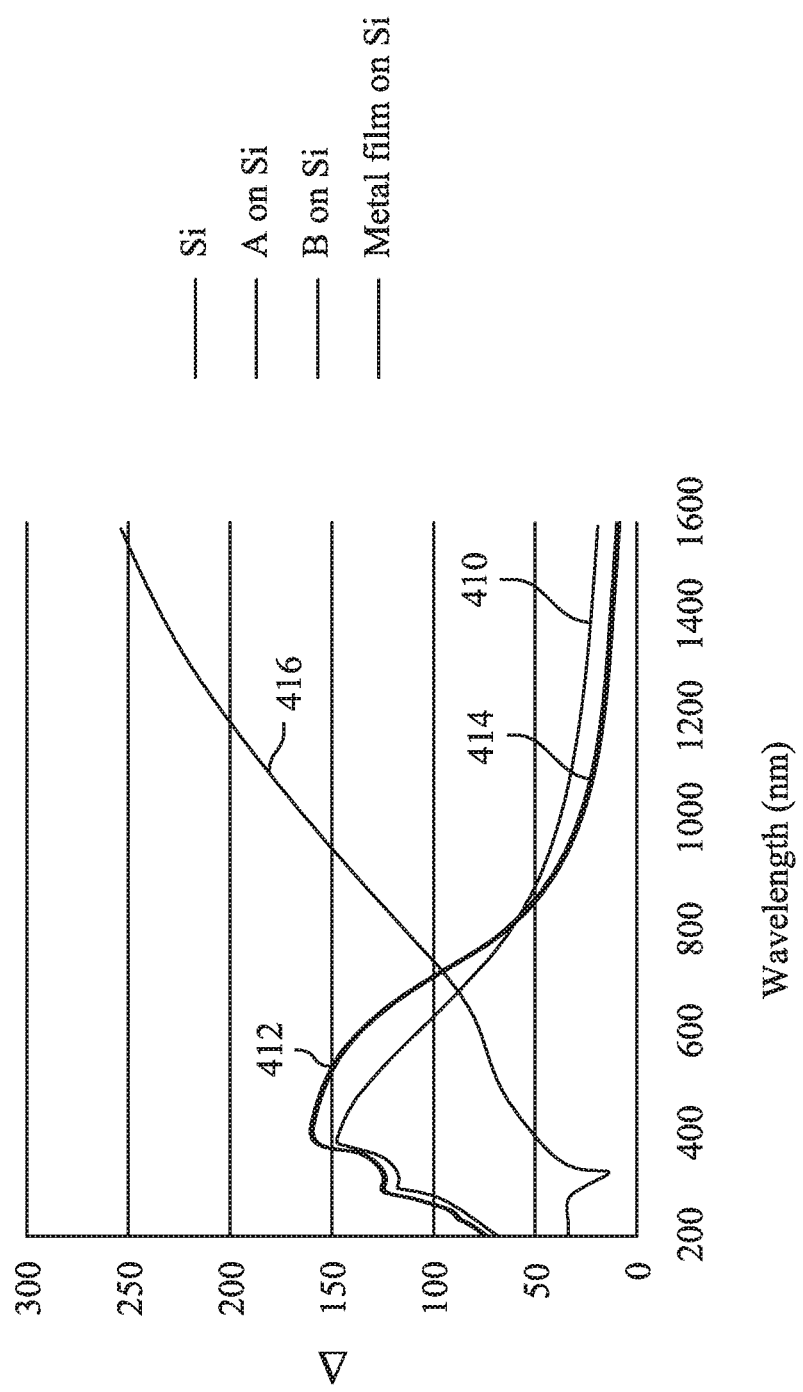

For example, FIG. 13A illustrates the amplitude ψ of silicon (line 400), the amplitude ψ of silicon polluted with a first residue A (line 402), the amplitude ψ of silicon polluted with a second residue B (line 404), and the amplitude ψ of a metal film (line 406). FIG. 13B illustrates the phase difference Δ of silicon (line 410), the phase difference Δ of silicon polluted with the first residue A (line 412), the phase difference Δ of silicon polluted with the second residue B (line 414), and the phase difference Δ of the metal film (line 416). It is shown in FIGS. 13A and 13B that with the change of the materials and the residue, the amplitude and the phase difference (in combination referred to the complex dielectric function) change accordingly, and hence the amplitude and the phase difference may indicate what materials are present on the surface of wafer.

In accordance with some embodiments of the present disclosure, a clean wafer (identical to wafer 18) may be measured using ellipsometry to generate a reference complex dielectric function. If residues are present at the surface of wafer 18, the complex dielectric function will deviate from the reference complex dielectric function, and hence comparing the complex dielectric function of wafer 18 with the reference complex dielectric function will reveal whether residue exist or not.

Figure 15:
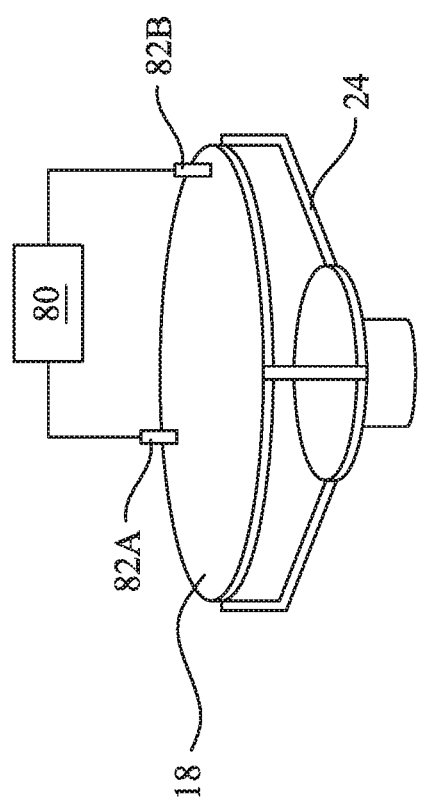
FIG. 15 illustrates determining the cleanness of a wafer by measuring surface charge in accordance with some embodiments.

In accordance with some embodiments of the present disclosure, the surface charge on the surface of wafer 18 is measured, and the result is used to determine the cleanness of wafer 18. Referring to FIG. 15, voltmeter 80 is connected to probes 82 (including 82A and 82B) that are in contact with the surface of wafer 18. Probes 82 are in contact with different portions of wafer 18. For example, probe 82A may be in contact with the center of the top surface of wafer 18, and probe 82B may be in contact with the edge of the top surface of wafer 18. A voltage is read from voltmeter 80. In accordance with some embodiments, the voltage is used to determine the cleanness of a wafer whose entire top surface is formed of a same material such as silicon, a metal, a dielectric material, etc.

Figure 16A:
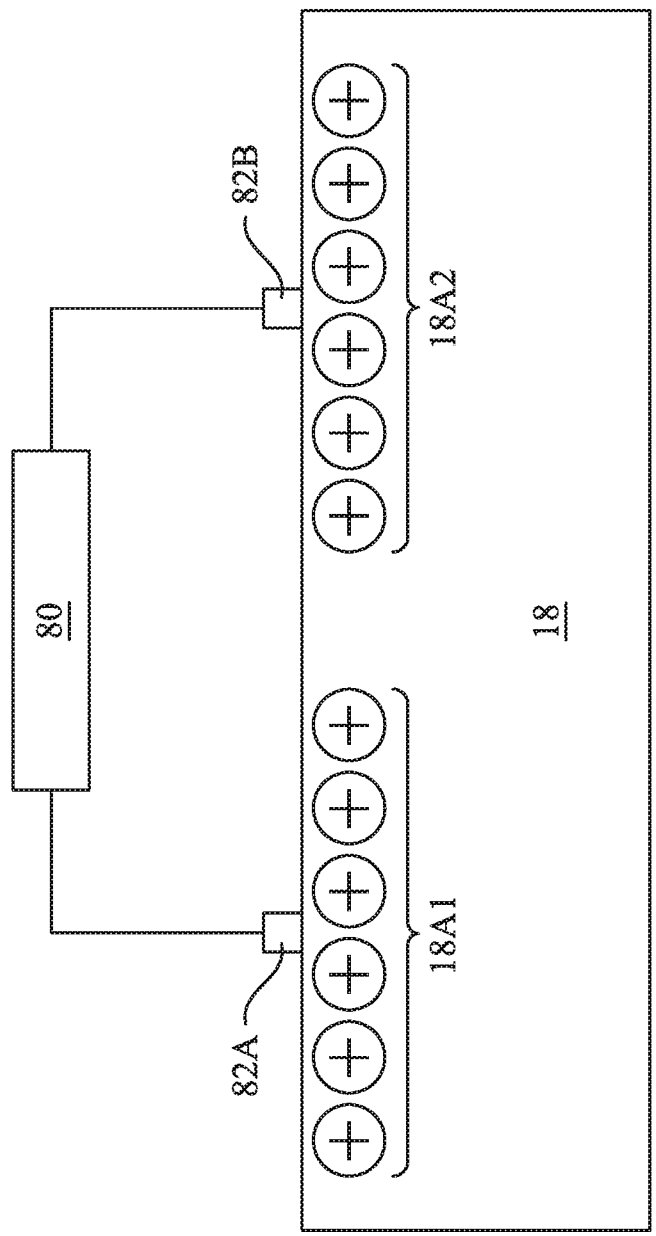
FIGS. 16A and 16B illustrate measuring the surface charge of wafers with different surface conditions in accordance with some embodiments.
Figure 16B:
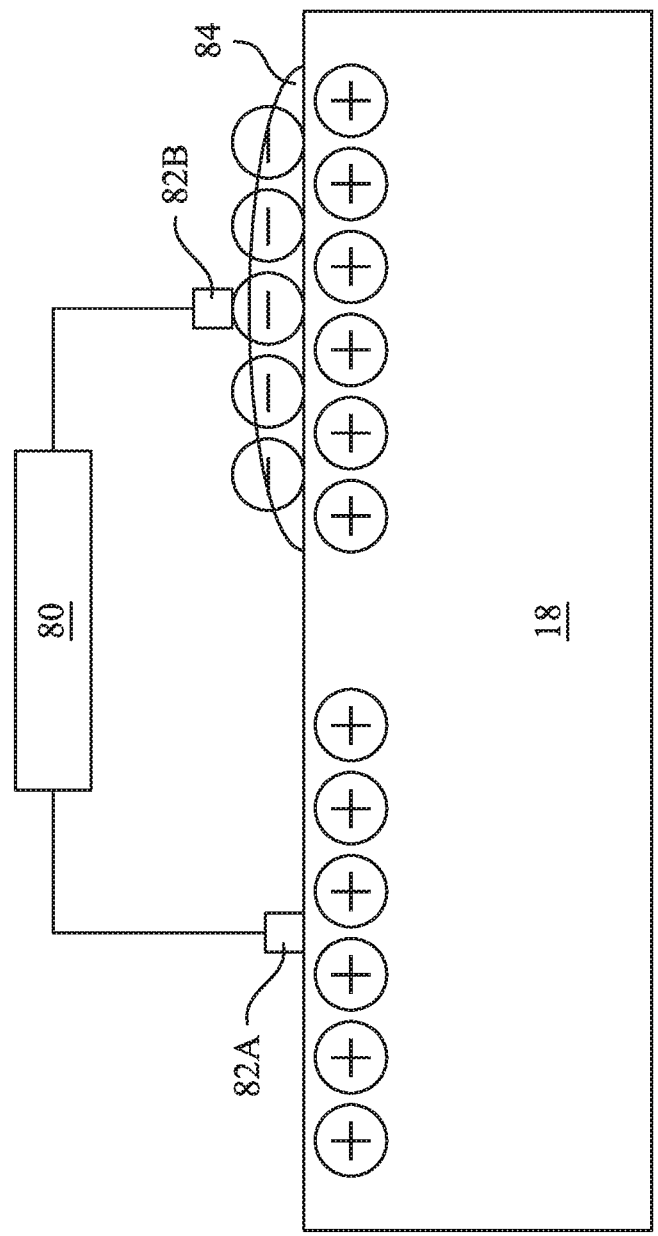

FIGS. 16A and 16B schematically illustrate that the surface charges of wafer 18 may be changed due to the cleanness of wafer 18, and the resulting voltage read from voltmeter 80 changes accordingly. For example, referring to FIG. 16A, when a clean wafer 18 is probed, voltmeter will have the result of 0 volt (or within $\pm\Delta V$, which is caused by variation) since the two terminals 82A and 82B are in contact with surface regions 18A1 and 18A2 that have the same surface conditions. For example, in FIG. 16A, the surface charges of both regions 18A1 and 18A2, which are in contact with probes 82A and 82B, are both clean and have positive charges accumulated. The voltage read from voltmeter 80 is thus within $\pm\Delta V$. If surface conditions of regions 18A1 and 18A2 are different from each other due to one or both regions 18A1 and 18A2 have residues, then the surface charges may change, resulting in the result of voltmeter 80 to be out of the range $\pm\Delta V$. For example, in the example shown in FIG. 16B, due to the existence of residue 84, negative charges are accumulated in region 18A2, causing a voltage difference between surface regions 18A1 and 18A2. Accordingly, voltmeter 80 will read a voltage having an amplitude greater than the variation $\pm\Delta V$, indicating the wafer 18 is not clean.

Figure 17:
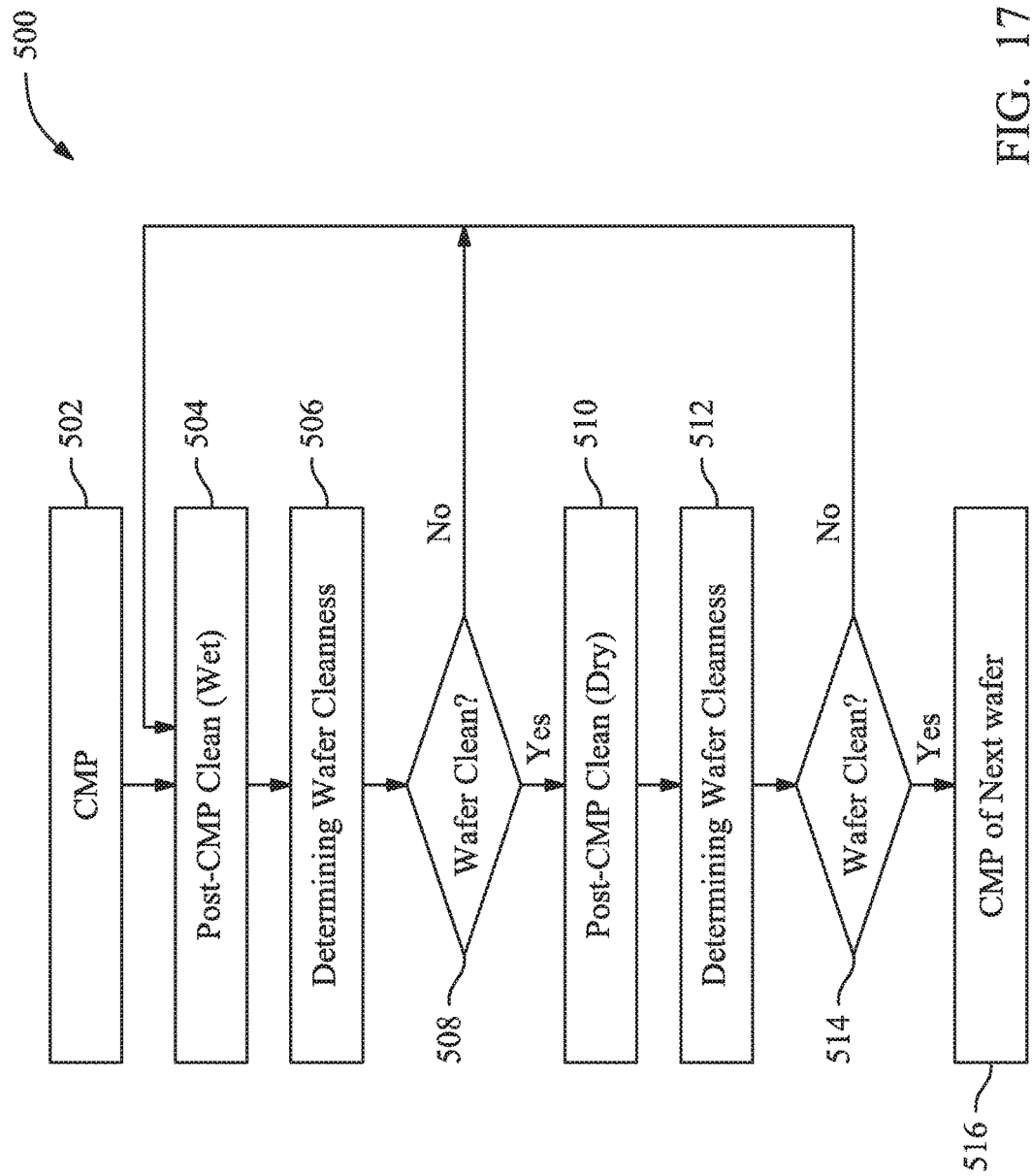
FIG. 17 illustrates a process flow of a CMP process and the post-CMP cleaning in accordance with some embodiments.

In the embodiments as shown in FIGS. 4 through 16B, when wafer 18 is found not clean, wafer 18 may go through the steps shown in FIGS. 2 and 3 again, as shown by step 514 in the process flow in FIG. 17. When wafer 18 is being checked for cleanness, other wafers are blocked, and no post-CMP cleaning is performed on the subsequent wafers, until wafer 18 is eventually determined as clean. Otherwise, if wafer 18 is found to be clean, the post-CMP is finished, and next wafer may be sent in for the post-CMP (step 516). Furthermore, if a plurality of wafers 18 is found to be not clean, the cleaning process may be adjusted, for example, the chemical solution clean and/or the rinsing process may be prolonged.

The embodiments of the present disclosure have some advantageous features. The determining of the cleanness of the wafer ensures that the wafer sent out of the CMP station is clean. In conventional post-CMP cleanness, a wafer may be taken out of the post-CMP apparatus for inspection. When the inspection is finished and it is determined that the wafer is not clean, a plurality of other wafers may have already undertaken the CMP process and the post-CMP cleaning, and may have been transported away, even if these wafers are not clean.

In accordance with some embodiments of the present disclosure, a method includes performing CMP on a wafer, placing the wafer on a chuck, performing a post-CMP cleaning on the wafer, and determining cleanness of the wafer when the wafer is located on the chuck.

In accordance with some embodiments of the present disclosure, a method includes performing CMP on a wafer, performing a post-CMP cleaning on the wafer using a chemical solution, rinsing the wafer with water, and determining cleanness of the wafer by checking waste water generated in the rinsing the wafer.

In accordance with some embodiments of the present disclosure, a method includes performing CMP on a wafer, performing a post-CMP cleaning on the wafer using a chemical solution, rinsing the wafer with water, drying the wafer, and after the drying the wafer, determining cleanness of the wafer by generating an FTIR spectrum or a Raman spectrum from the wafer.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method comprising:
    performing Chemical Mechanical Polish (CMP) on a wafer;
    performing a post-CMP cleaning on the wafer using an acidic or a base solution;
    rinsing the wafer using De-ionized (DI) water;
    opening a first valve to direct waste water rinsed off from the wafer to a water collecting unit, wherein a second valve is turned off when the first valve is opened;
    after the first valve is opened for a period of time, turning off the first valve;
    with the first valve being turned off, opening a second valve to direct the waste water rinsed off from the wafer through a transparent cell; and
    determining cleanness of the wafer by determining cleanness of the DI water rinsed off from the wafer, wherein the determining the cleanness of the DI water rinsed off comprises determining number of particles having sizes greater than a pre-specified size in the DI water rinsed off from the wafer.

2. The method of claim 1, wherein the wafer is determined as not clean, and the method further comprises performing an additional post-CMP cleaning on the wafer.

3. The method of claim 1, wherein when the determining cleanness of the wafer is performed, other wafers are blocked from having CMP performed.

4. The method of claim 1, wherein the determining cleanness of the wafer is performed when the wafer is rinsed.

5. The method of claim 4, wherein the cleanness of the DI water is checked using a laser particle counter.

6. The method of claim 4, wherein the cleanness of the DI water is checked using dynamic laser scattering.

7. A method comprising:
performing Chemical Mechanical Polish (CMP) on a wafer;
performing a post-CMP cleaning on the wafer using a chemical solution;
starting rinsing the wafer with water;
delaying a period of time after the rinsing the wafer is started, wherein during the period of time, waste water rinsed off from the wafer is collected into a water collecting unit; and
after the period of time is passed, determining cleanness of the wafer by checking waste water generated in the rinsing the wafer.

8. The method of claim 7, wherein when the period of time is being delayed, the waste water rinsed off from the wafer is directed through a first valve to the water collecting unit.

9. The method of claim 8, wherein after the period of time is passed, the waste water rinsed off from the wafer is redirected through a second valve to a device for determining the cleanness of the wafer.

10. The method of claim 7, wherein the checking waste water is performed using a laser particle counter.

11. The method of claim 7, wherein the checking waste water is performed using dynamic laser scattering.

12. A method comprising:
performing Chemical Mechanical Polish (CMP) on a wafer;
performing a post-CMP cleaning on the wafer;
after the post-CMP cleaning, rinsing the wafer with water;
opening a first valve to direct waste water rinsed off from the wafer to a water collecting unit, wherein a second valve is turned off when the first valve is opened;
after the first valve is opened for a period of time, turning off the first valve;
with the first valve being turned off, opening a second valve to direct waste water rinsed off from the wafer through a transparent cell; and
determining cleanness of the wafer by checking the waste water passing through the transparent cell.

13. The method of claim 12, wherein the cleanness of the wafer is determined using a laser particle counter.

14. The method of claim 12, wherein the cleanness of the wafer is determined using dynamic laser scattering.

15. The method of claim 1, wherein the determining cleanness of the wafer is performed after the wafer is rinsed for a pre-determined period of time.

16. The method of claim 15 further comprising finding the pre-determined period of time, and the finding comprising:
performing CMP on a plurality of sample wafers;
selecting a delay duration for each of the plurality of sample wafers, wherein the delay durations of the plurality of sample wafers are different from each other;
start rinsing the plurality of sample wafers;
determining cleanness of the plurality of sample wafers after the delay durations of respective ones of the plurality of sample wafers; and
selecting the pre-determined period of time as being one of the delay durations long enough for a respective one of the plurality of sample wafers is clean.

17. The method of claim 7, wherein during a time starting from a first time the wafer starts to be rinsed and ending at a time after the period of time elapses, the waste water is directed to different paths.

18. The method of claim 7, wherein the cleanness of the wafer is determined by checking number of particles having sizes greater than a pre-specified size.

19. The method of claim 12, wherein the cleanness of the wafer is determined by checking number of particles having sizes greater than a pre-specified size.

20. The method of claim 9, wherein when the first valve is opened for directing the waste water to the water collecting unit, the second valve is closed, and when the second valve is opened for redirecting the waste water, the first valve is closed.

* * * * *